(12) United States Patent
Goldstein et al.

(10) Patent No.: US 11,364,128 B2
(45) Date of Patent: Jun. 21, 2022

(54) ARTHRITIS PLATE

(71) Applicant: Medline Industries, LP, Northfield, IL (US)

(72) Inventors: Scott Goldstein, Chicago, IL (US); Wes Reed, Libertyville, IL (US)

(73) Assignee: MEDLINE INDUSTRIES, LP, Northfield, IL (US)

( * ) Notice: Subject to any disclaimer, the term of this patent is extended or adjusted under 35 U.S.C. 154(b) by 877 days.

(21) Appl. No.: 15/620,225

(22) Filed: Jun. 12, 2017

(65) Prior Publication Data

US 2018/0353301 A1 Dec. 13, 2018

(51) Int. Cl.
*A61F 2/42* (2006.01)
*A61B 17/80* (2006.01)
*A61F 2/30* (2006.01)
*A61B 17/17* (2006.01)

(52) U.S. Cl.
CPC ........ *A61F 2/4225* (2013.01); *A61B 17/8014* (2013.01); *A61B 17/8061* (2013.01); *A61B 17/1728* (2013.01); *A61B 17/8052* (2013.01); *A61F 2002/30578* (2013.01); *A61F 2002/30754* (2013.01); *A61F 2002/30777* (2013.01); *A61F 2002/30787* (2013.01); *A61F 2002/30902* (2013.01); *A61F 2002/4233* (2013.01); *A61F 2230/0004* (2013.01)

(58) Field of Classification Search
CPC ............ A61F 2/4225; A61F 2002/4233; A61F 2002/30578; A61F 2002/30754; A61F 2002/30777; A61F 2002/30787; A61F 2002/30902; A61F 2230/0004; A61B 17/80; A61B 17/8014; A61B 17/8061; A61B 17/1728; A61B 17/8052
See application file for complete search history.

(56) References Cited

U.S. PATENT DOCUMENTS

| | | | |
|---|---|---|---|
| 7,291,175 B1 * | 11/2007 | Gordon | A61F 2/4225 606/98 |
| 7,909,880 B1 * | 3/2011 | Grant | A61F 2/4225 623/21.19 |
| 9,788,873 B2 * | 10/2017 | Bottlang | A61B 17/863 |
| 2004/0093081 A1 * | 5/2004 | Nilsson | A61L 27/58 623/13.18 |
| 2004/0260291 A1 * | 12/2004 | Jensen | A61B 17/1728 606/915 |
| 2009/0177203 A1 * | 7/2009 | Reiley | A61B 17/8095 606/87 |

(Continued)

*Primary Examiner* — Jerrah Edwards
*Assistant Examiner* — Melissa A Hoban
(74) *Attorney, Agent, or Firm* — Fitch, Even, Tabin & Flannery LLP

(57) ABSTRACT

Disclosed are orthopedic implant kits. One disclosed kit comprises an implant having a joint head portion, the joint head portion having a generally convex distal surface and generally concave proximal surface, the implant comprising a post portion protruding proximally from the proximal surface, the post portion having a dorsal surface and a ventral surface (which is a plantar surface in the case of a metatarsal bone) and including a first threaded aperture extending therebetween, and a bone screw. The bone screw has a threaded shaft complementary to the threaded surface of the post portion and preferably is configured to provide bicortical fixation of the implant.

5 Claims, 7 Drawing Sheets

(56) References Cited

U.S. PATENT DOCUMENTS

| | | | | |
|---|---|---|---|---|
| 2010/0262254 A1* | 10/2010 | Lawrence | ............ | A61F 2/4225 |
| | | | | 623/21.19 |
| 2011/0093085 A1* | 4/2011 | Morton | ................. | A61B 17/15 |
| | | | | 623/21.19 |
| 2013/0090695 A1* | 4/2013 | Bernstein | ............ | A61B 17/808 |
| | | | | 606/281 |
| 2013/0197638 A1* | 8/2013 | Clifford | ................. | A61B 17/68 |
| | | | | 623/13.12 |
| 2014/0018812 A1* | 1/2014 | Graham | ............ | A61B 17/1739 |
| | | | | 606/87 |
| 2014/0180343 A1* | 6/2014 | Gaudin | ............ | A61B 17/8061 |
| | | | | 606/283 |
| 2014/0316530 A1* | 10/2014 | Early | ................... | A61F 2/4225 |
| | | | | 623/21.19 |
| 2017/0042688 A1* | 2/2017 | Maale | ................... | A61F 2/4081 |
| 2017/0049576 A1* | 2/2017 | Guilford | ............... | A61F 2/3094 |
| 2017/0367838 A1* | 12/2017 | Cavanagh | ............ | A61F 2/4225 |
| 2018/0296257 A1* | 10/2018 | Penzimer | ............ | A61B 17/8004 |
| 2018/0318097 A1* | 11/2018 | Armacost | ............ | A61F 2/4225 |

\* cited by examiner

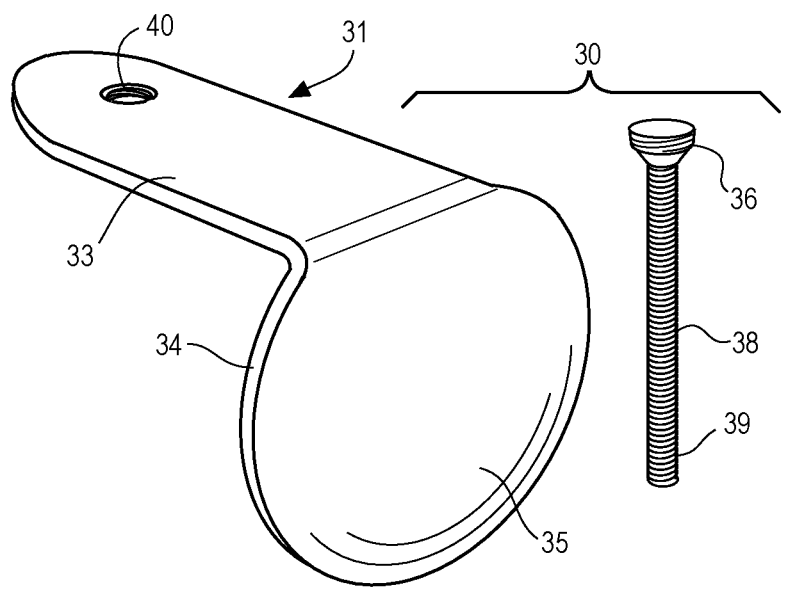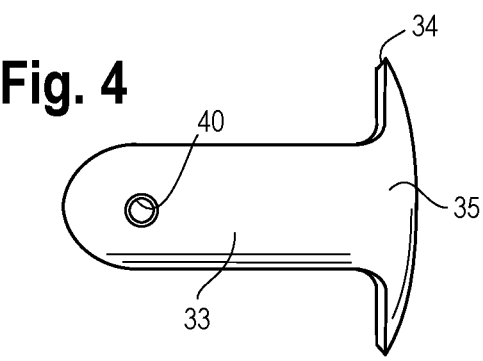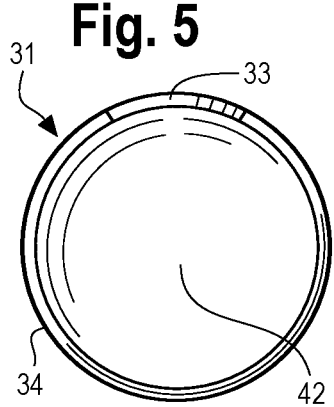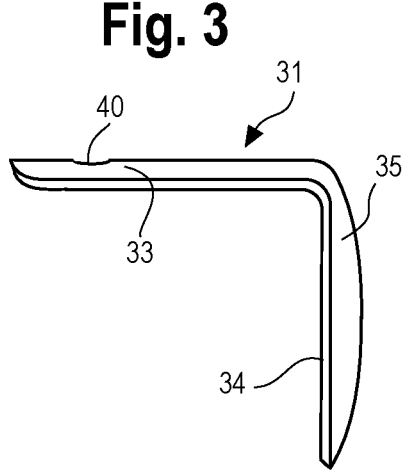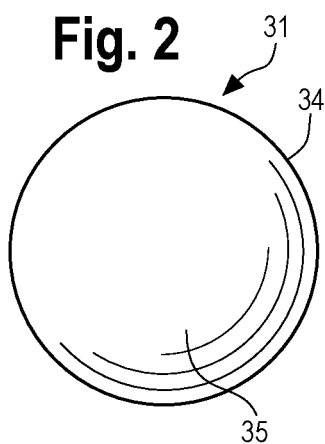

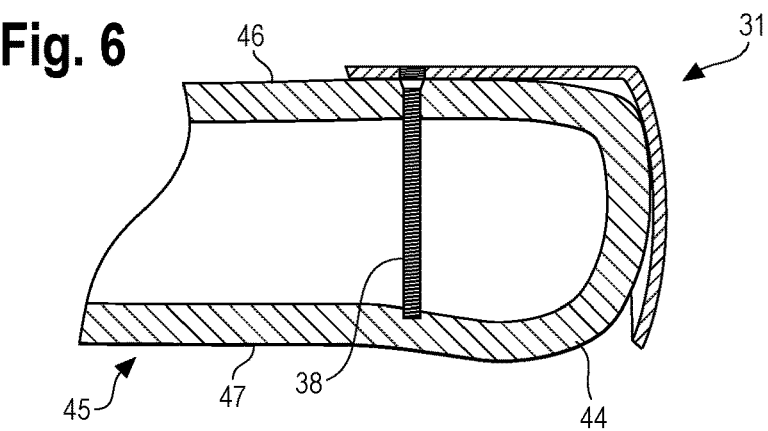
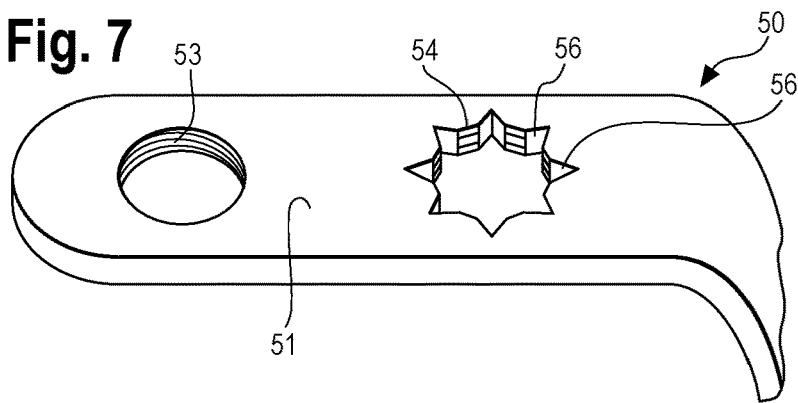
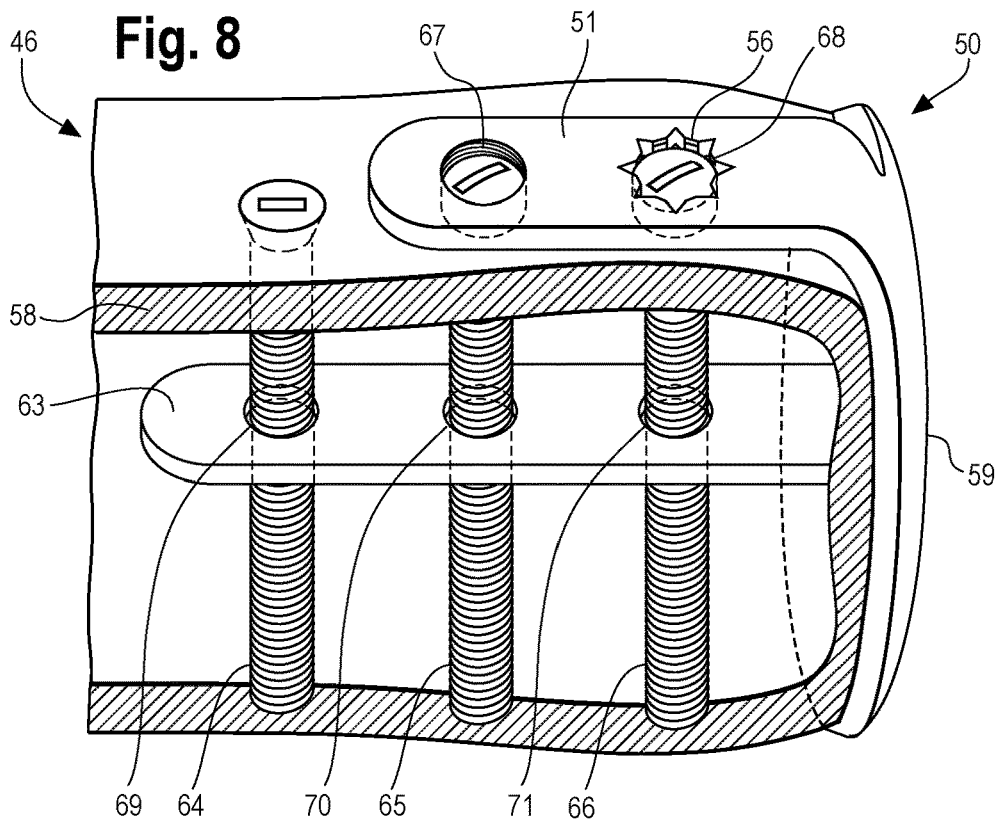

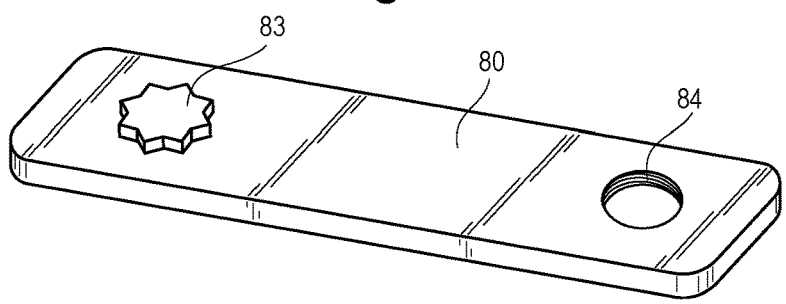
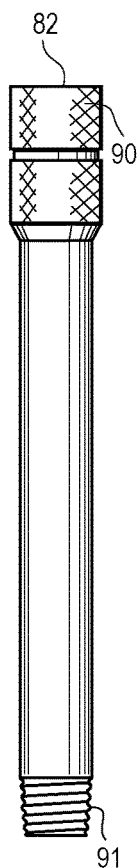
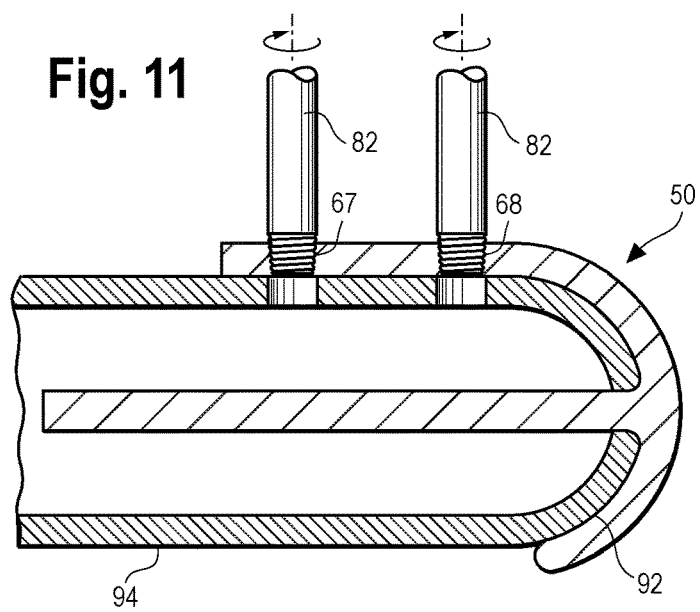
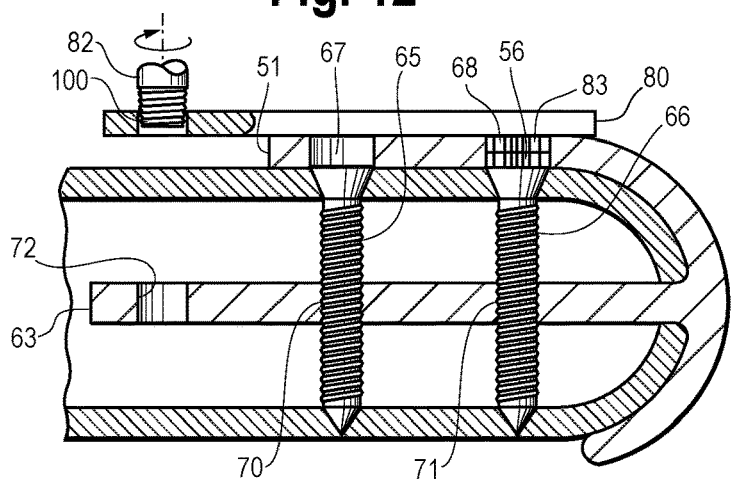

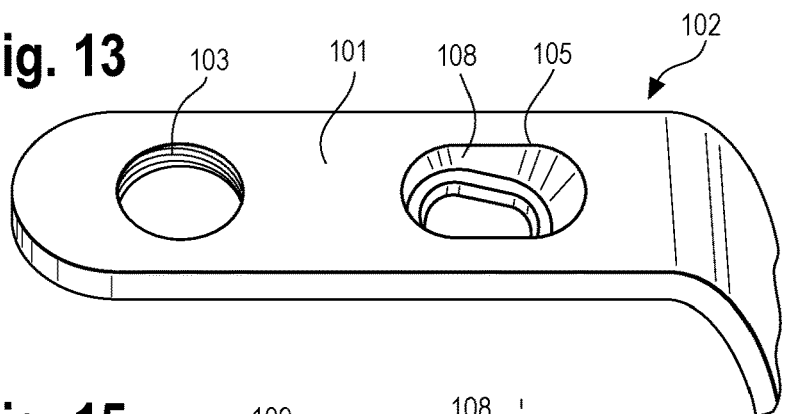
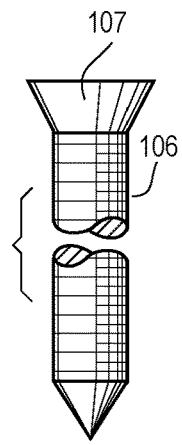
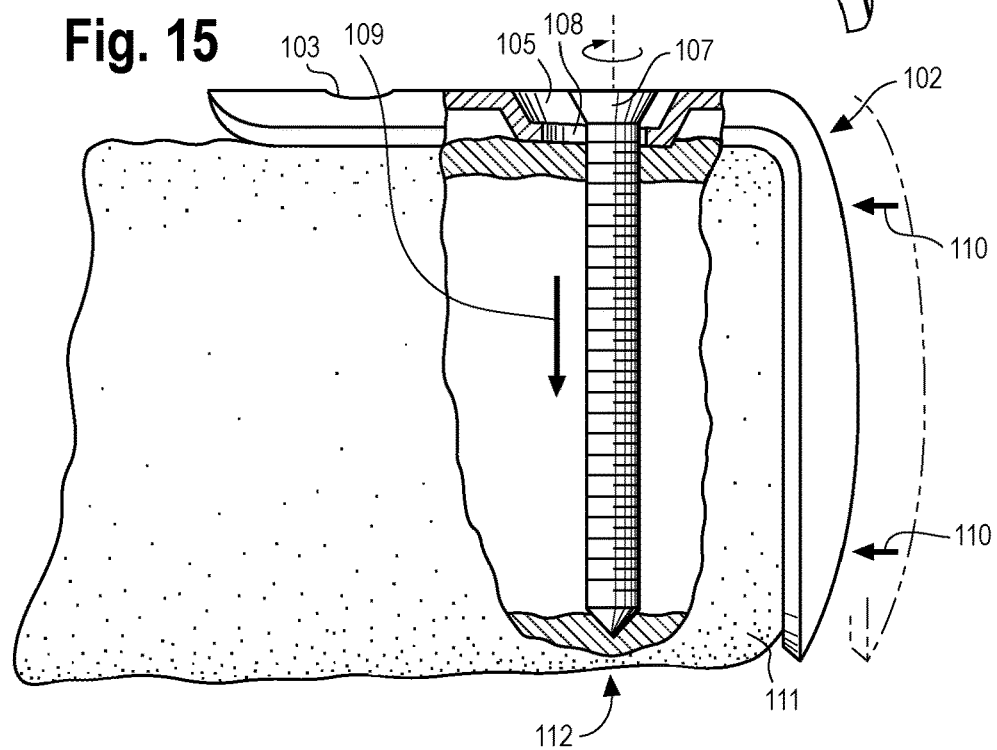
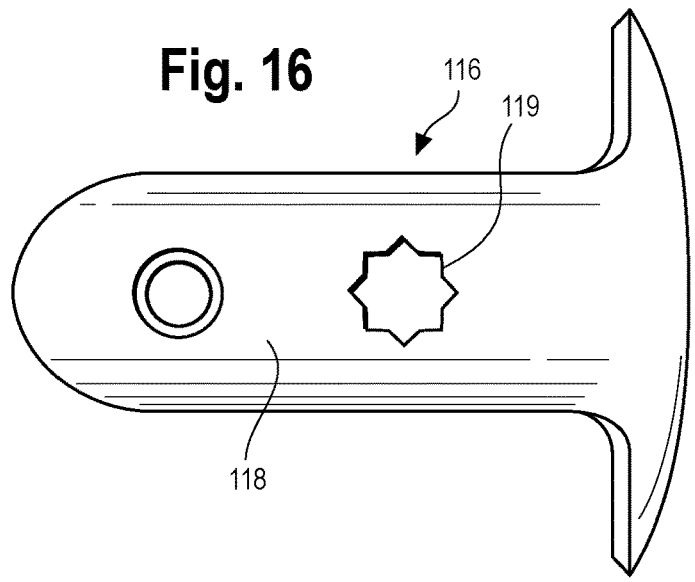

ARTHRITIS PLATE

TECHNICAL FIELD

The invention is in the field of implants for joint replacements, and in certain embodiments is in the field of implants useful for hallux metatarsophalangeal arthroplasty.

BACKGROUND OF THE INVENTION

The metatarsophalangeal articulations are the joints between the metatarsal bones of the foot and the proximal phalanges of the toes, including the hallux. These are condyloid joints that engage shallow cavities of the proximal phalanges. In patients with arthritis, these joints can become inflamed or otherwise damaged. It is known to install a silicone implant in the region of the metatarsal joint head. Because the metatarsophalangeal articulations are subject to tremendous stresses incurred by walking, it is known that silicone implants are is prone to degradation and failure.

Another known procedure is the fusion of the metatarsal bone and hallux. This procedure creates a fused bone structure in place of the natural joint, and limits the patient's natural range of motion. In some cases, a silicone implant is installed in an attempt to avoid fusion, but fusion ultimately may be required upon failure of the silicone implant.

Numerous metallic metatarsal head implants also are known. These implants are not generally subject to degradation as with silicone implants, but in light of the tremendous stresses applied to the metatarsal bone they can become dislodged, again, ultimately leading to the necessity of joint fusion therapy.

It has now been found that the implant having a head portion and at least one of a dorsal plate portion or post portion, in some embodiments both a plate portion and a post portion, may be provided. The implant is provided in a kit with at least one screw that is used to secure the implant through the dorsal portion or plate portion and that, in preferred embodiments, is used to provide bicortical fixation as described in more detail hereinbelow.

BRIEF DESCRIPTION OF THE DRAWINGS

FIG. 1 is a perspective view of an orthopedic implant kit in accordance with one embodiment, the kit including an implant and a bone screw.

FIG. 2 is a front elevational view of the implant shown in FIG. 1.

FIG. 3 is a side elevational view of the implant shown in FIG. 1.

FIG. 4 is a top plan view of the implant shown in FIG. 1.

FIG. 5 is a rear elevation view of the implant shown in FIG. 1.

FIG. 6 is a side elevational view, partially cut away, of a metatarsal bone and depicting the orthopedic implant kit of FIG. 1 shown in use to repair the head of the bone.

FIG. 7 is a perspective view of the dorsal plate portion of an orthopedic implant in accordance with a second embodiment, enlarged relative to FIG. 1.

FIG. 8 is a side view in representation, partially cut away, of a metatarsal bone showing the orthopedic implant of FIG. 7 and depicting three screws.

FIG. 9 is a bottom perspective view of a target guide useful in conjunction with the implant depicted in FIG. 7.

FIG. 10 is a side elevational view of a uniaxial drill guide suitable for use with the implant shown in FIG. 7 and the target guide shown in FIG. 9.

FIG. 11 is a side sectional view depicting the process of installing the implant depicted in FIGS. 7 and 8, showing the use of uniaxial drill guides to position two of the screws shown in FIG. 8.

FIG. 12 depicts a subsequent step in the process of installing the implant depicted in FIGS. 7 and 8, showing the target guide and its use to position a uniaxial drill guide for positioning of the third screw shown in FIG. 8.

FIG. 13 is a perspective view of the dorsal plate portion of an orthopedic implant in accordance with another embodiment, depicting a compression aperture in the dorsal plate.

FIG. 14 is a side elevational view of bone screw suitable for use with the implant shown in FIG. 13.

FIG. 15 is a side elevational view, partially cut away, of a metatarsal bone and depicting a kit that includes the implant shown in FIG. 13 and the bone screw shown in FIG. 14. FIG. 15 depicts a first step in the installation of the implant in a metatarsal bone.

FIG. 16 is a top plan view of an implant in accordance with another embodiment.

Figure 17:
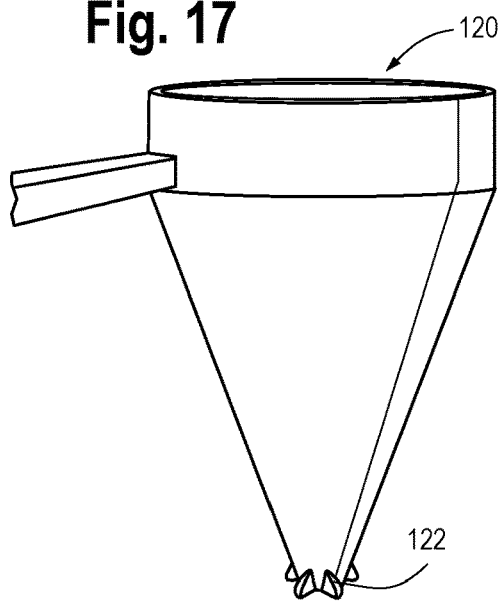
FIG. 17 is a side elevation of a polyaxial drill guide suitable for use with the implant of FIG. 16.

References to "top, "side," and the like in the figures are for convenient reference to the drawings, because in practice the implant may be rotated when in use omnidirectionally. "Top" views generally connote views of the dorsal region of the metatarsal bone.

DETAILED DESCRIPTION

Generally, in one embodiment, an orthopedic implant kit comprises an implant having a joint head portion, the joint head portion having a generally convex distal surface and generally concave proximal surface, the implant comprising a post portion protruding proximally from the proximal surface, the post portion having a dorsal surface and a ventral surface (which is a plantar surface in the case of a metatarsal bone) and including a first threaded aperture extending therebetween, and a bone screw. The bone screw has a threaded shaft complementary to the threaded surface of the post portion and preferably is configured to provide bicortical fixation of the implant. The implant is not limited to use in metatarsal bones, but will be described in connection with metatarsal phalangeal arthroplasty as one specific embodiment. The implant post portion preferably takes the form of a flat blade, and may include a plurality of threaded apertures each extending between the dorsal surface and ventral surface, whereby the kit will include a plurality of bone screws complementary to at least one of the threaded apertures and each configured to provide bicortical fixation. In some embodiments the implant also includes an external plate portion, which can be a dorsal plate portion in the case of a metatarsal bone implant. The dorsal plate portion also protrudes proximally from the proximal surface. This dorsal plate portion may have various configurations and may include, for example, a first keyed structure, optionally with a dorsal plate aperture juxtaposed therewith, and a dorsal plate aperture that is not juxtaposed with the keyed structure.

In another embodiment, not mutually exclusive with respect to the first embodiment heretofore described, the kit may include the implant having a joint head portion and having a generally convex distal surface and a generally concave proximal surface, a dorsal or other external plate portion protruding proximally from the proximal surface, where the dorsal plate portion includes at least a first dorsal plate aperture extending therethrough, the kit further including a first bone screw. The bone screw has a threaded shaft that is sized to fit through the first dorsal plate aperture and configure to provide bicortical fixation of the implant. The aperture may be a threaded aperture having a threaded locking structure, wherein a bone screw has a threaded head that is complementary to the threading of the threaded locking aperture.

With reference to FIG. 1, the kit 30 in the illustrated embodiment includes an implant 31 having a dorsal plate portion 33 that protrudes proximally from the proximal surface of the joint head portion 34. The joint head portion 34 has a generally convex distal surface 35 and a generally concave proximal surface (not shown in FIG. 1). The kit further includes a screw 38 that has threading 39 that is designed to engage cortical bone in the dorsal and plantar areas of the metatarsal bone. The screw 38 further has a threaded head 36 that engages a threaded aperture 40 in the dorsal plate portion 33 of the implant 31. FIGS. 2-5 further illustrate the implant 31 and the generally concave proximal surface 42 of the joint head portion 34 is shown in FIG. 5.

With reference now to FIG. 6, it is seen that the implant 31 is secured to the head portion 44 of a metatarsal bone 45 via the screw 38, a portion of which engages the dorsal cortical bone 46 and a portion of which engages the plantar cortical bone 47. In placing the implant, before or after the implant has been placed on the head of the metatarsal bone, a surgeon drills an appropriate shaft through the bone to the plantar aspect of the cortical bone and then installs the screw to secure the implant in place.

With reference to the alternative implant 50 depicted in FIG. 7, the dorsal plate portion 51 is provided in this embodiment with two threaded apertures, 53 and 54. Threaded aperture 54 has a keyed region 56, generally star-shaped in the illustrated embodiment, wherein the threads are interrupted by the keyed structure. This implant 50 is intended to be installed in the metatarsal bone 58 illustrated in FIG. 8. As seen, the implant 50 has a joint head portion 59 and proximally protruding dorsal plate portion 51 and post portion 63. The implant 50 is secured via the use of three screws 64, 65, and 66. Screws 65 and 66 extend respectively through apertures 67 and 68 in the dorsal plate portion and are threaded through correspondingly sized apertures 70 and 71 in the post portion 63. In this embodiment the third screw 64 is secured bicortically to the bone 58 and is also secured to the post portion 63 via threaded engagement with the threaded aperture 69 in the post portion 63. As seen, the first dorsal plate aperture 67 is not juxtaposed with the keyed region 56 and the second dorsal plate aperture 68 is juxtaposed with the keyed region. Various other configurations are possible.

Generally, it will be necessary for a surgeon to pre-drill pilot holes into the bone to place the screws 64, 65, 66. Because each of the screws engages the post portion 63 and is secured thereto via the threaded apertures 69, 70, 71, it is generally necessary to ensure that the pilot holes align positionally and coaxially with the corresponding apertures in the post portion. For this purpose, the target guide 80 shown at FIG. 9 and one or more drill guides (one shown as drill guide 82 in FIG. 10) are provided, it being recognized that the kit may include plural drill guides of the type illustrated in FIG. 10. As seen in FIG. 9, the target guide 80 includes a protruding star-shaped boss 83. The boss 83 comprises a keyed structure that is engageable with the keyed region 56 on the dorsal plate portion 51. While the illustrate embodiment depicts a generally star-shaped boss and corresponding region, the keyed structure and region may take other suitable forms. The drill guide 82 illustrated in FIG. 10 includes a knurled handle 90 and a threaded end 91. The threaded end 91 is intended to engage the threaded apertures 67, 68, of the dorsal plate portion 51 illustrated in FIG. 8.

In this embodiment, installation of the implant is depicted in FIGS. 11-12. As seen therein, the implant 50 is placed over the head portion 92 of the metatarsal bone 94. The surgeon may route a region of the dorsal area of the bone to accommodate the dorsal plate portion 51. Thereafter, drill guide 82 (or alternatively the same drill guide used sequentially) are threaded into apertures 67, 68 in the dorsal plate portion 51. Using a drill, a surgeon inserts a properly sized drill bit (not shown) through each drill guide 82 to ensure proper placement and axial alignment of the drilled shaft. Subsequently, as depicted in FIG. 12, screws 65, 66 are screwed into apertures 67, 68 respectively, whereupon they engage the post portion 63 at threaded apertures 70, 71. Before or after these screws 65, 66 are installed, the target guide 80 is placed over the dorsal plate portion 51 with the star-shaped boss 83 engaging corresponding keyed region 56 in the dorsal plate portion 51 thereby serving as a key to position and orient the drill shaft for the third bone screw (not shown in FIG. 12). A drill guide 82 is threaded into the aperture 100 to ensure proper axial alignment of the shaft with the threaded aperture 72 in the post portion 63. In this manner, proper placement and orientation of all three bone screws can be ensured.

The dorsal plate portion apertures may take a number of alternative forms. For instance, as illustrated in FIG. 13, the dorsal plate portion 101 of the implant 102 may have a locking slot 103 with threads to engage the threaded head end of a screw, and also may include a non-locking, compression aperture that takes the form of a ramped slot 105. This latter slot 105 is suitable for use with the screw 106 shown in FIG. 14, which has no threads in the head end 107 of the screw but which instead is formed with an inclined profile. In use, as seen in FIG. 15, the non-locking compression screw is installed first. The screw head end 107 engages the ramped surface 108 of the slot 105. As the screw moves towards the plantar area in the direction of arrow 109, the engagement of the screw head and 107 and ramped surface 108 causes a compressive force, as represented by arrow 110, to be exerted on the implant 102 against the head portion 111 of the metatarsal bone 112. Subsequently, a second screw (not shown), this screw having a threaded head, may be inserted through threaded aperture 103.

Figure 18:
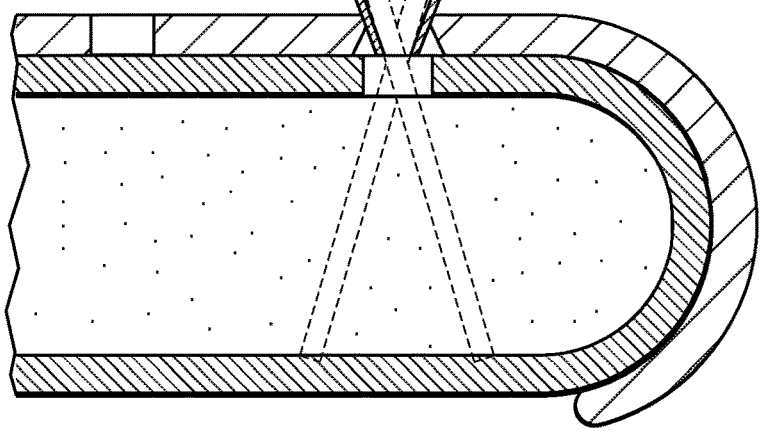
FIG. 18 is a side elevation, partially cut away, of a metatarsal bone illustrating the polyaxial drill guide of FIG. 17 positioned on the dorsal plate of the implant of FIG. 16 for installation thereof.
Figure 20:
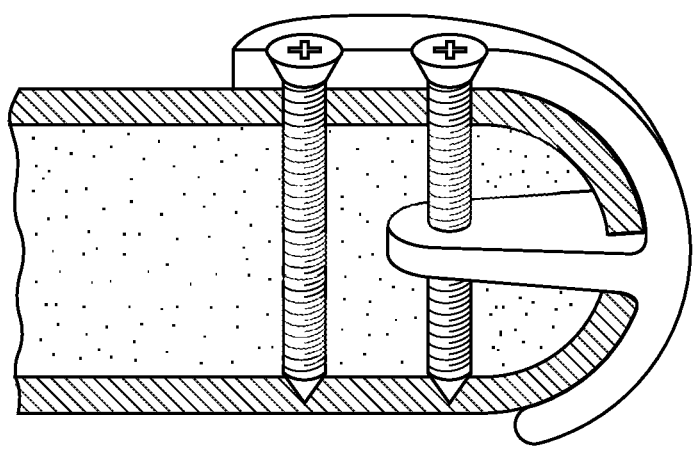
FIG. 20-24 are representational views depicting various alternative implant embodiments installed in metatarsal bone.
Figure 21:
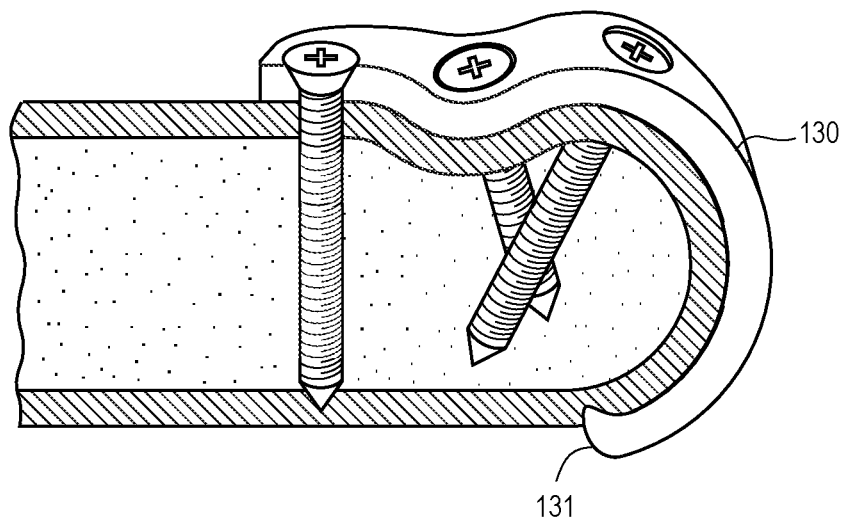
Figure 22:
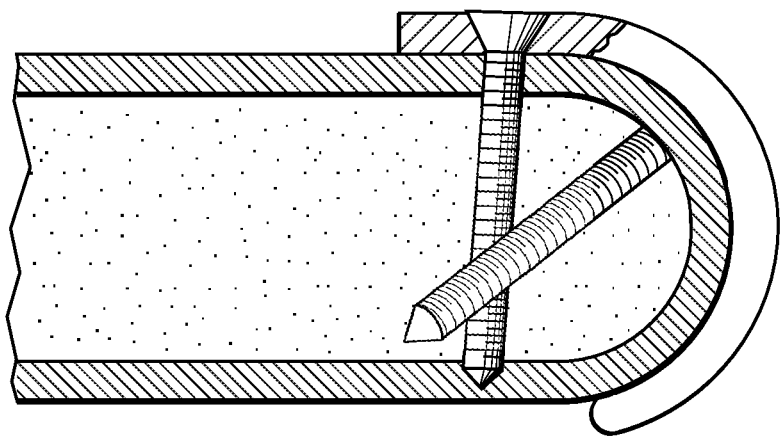
Figure 23:
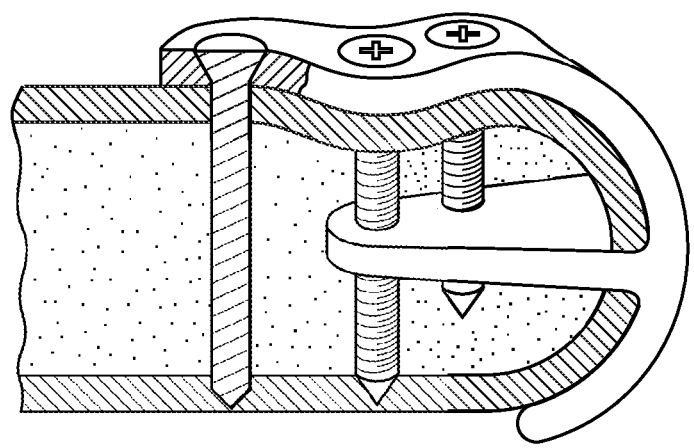
Figure 24:
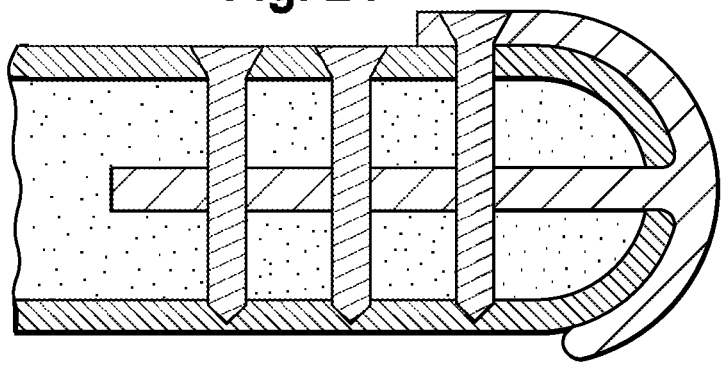

In another alternative embodiment, the implant 116 takes the form shown in FIG. 16, in which the dorsal plate portion 118 includes a keyed region 119. This is suitable for use with the polyaxial drill guide 120 shown in FIG. 17, which has a keyed bottom surface 122 that corresponds with the keyed region 119 shown in the implant 116 of FIG. 16. Via this construction, a bone screw may be screwed at various angles, within limits imposed by the polyaxial drill guide 120, as seen in FIG. 18 for drill bit 123. This embodiment is suitable for drilling a screw where there is no post portion in regions beneath the keyed region 119.

Figure 19:
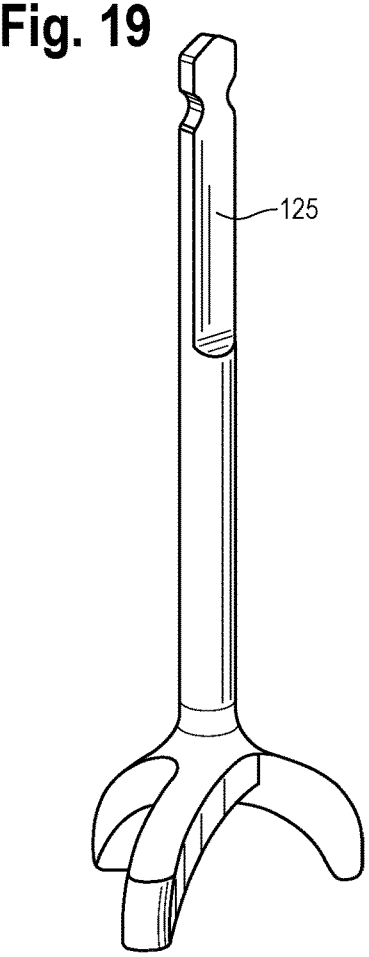
FIG. 19 is a perspective view of a bone reamer used to shape the head of a metatarsal bone in preparation for installation of an orthopedic implant.

The head portion of the implant is preferably composed of a cobalt chrome material. To ensure that the condyloid head portion fits within the hallux cavity of the patient, a reamer 125 as shown in FIG. 19, may be provided with the kit or as a separate component. The reamer 125 may be used to size and shape the head portion of the implant once it has been installed.

Various alternative embodiments are represented in FIGS. 20-24. With particularly reference to the embodiments shown in FIG. 21, the joint head portion 130 may terminate in a hook portion 131 for additional stability. The hook portion is not limited to the embodiment shown in FIG. 21, but to the contrary may be used in conjunction with other embodiments.

Numerous other features are contemplated. For example, it is contemplated that bone-engaging portions of the implant and optionally the screws may be coated with hydroxyapatite or another suitable bone biocompatible material.

When installing the implant, an elongate pathway is channeled into the end of the bone for insertion of the post portion of the implant, for those implants having a post portion. It is contemplated that the kit may include a cannulated slotting mechanism (not shown) for assistance in drilling a slot for the post-portion of implants that are provided with such portion. The post portion is inserted into the pathway and the bone screw is screwed through a first cortical surface of the bone, through an aperture in the dorsal plate portion where provided, and into a second cortical surface of the bone. The procedure may be facilitated by use of the target guide and drill guide as described previously. For implants without a post portion but having a dorsal plate portion, after the implant is placed into position, a bone screw is inserted through the aperture in the dorsal plate and into the bone in a manner that is sufficient to provide bicortical fixation. Generally, this contemplates insertion of the bone screw through the first dorsal plate aperture and through a first cortical surface of a bone and into a second cortical surface of the bone. Bicortical fixation is not always necessary, and is not necessary for each screw a multi-screw configuration, but it is preferable that each screw does provide bicortical fixation as described herein.

It is thus seen that an implant having a stable structure is provided. In practice, because the bones of a subject requiring the implant are expected to vary in size from patient to patient, the kit as supplied may include a plurality of screws of various lengths for each aperture. In various combinations, the implant has at least one of a post portion and a plate portion, and may have both a post portion and a plate portion. The plate portion may have as many aperture as the post portion or may have more apertures than the post portion; for instance, the plate portion may have one, two, three, or more apertures and the post portion may have one, two, three, or more apertures in any suitable permutation. The plate portion may extend proximally to the same distance as the post portion, or the plate portion may extend proximally to a greater distance than the post portion, or the post portion may extend proximally to a greater distance than the plate portion. The plate portion may have no keyed structure or may have one, two, or more than two key structures, particularly if the post portion extends proximally to a greater distance than the plate portion and has one or more additional apertures that require proper placement and orientation of a retaining screw.

In practice, the screws and implants and any suitable polyaxial or uniaxial drill guides and reamers may be supplied together or may be supplied separately. If the implant is supplied separately from the screws, the kit will be deemed to be provided or assembled in situ by the surgeon or hospital.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A method for placing an implant on a bone comprising the steps of:
    providing an orthopedic implant kit comprising:
        an implant, said implant having a joint head portion, said joint head portion having a distal surface and a proximal surface, said distal surface being generally convex prior to placement of the implant on said bone and said proximal surface being generally concave prior to placement of the implant on said bone;
        a dorsal plate portion protruding proximally from said proximal surface, wherein the dorsal plate portion includes at least a first dorsal plate aperture extending therethrough;
        a first bone screw having a threaded shaft, said threaded shaft being sized to fit through said first dorsal plate aperture, said first bone screw being configured to provide bicortical fixation of said implant;
    placing said implant onto the head of a bone; and
    inserting said first bone screw through said first dorsal plate aperture, through a first cortical surface of said bone, and into a second cortical surface of said bone.

2. The method of claim 1, wherein the bone is a metatarsal bone.

3. The method of claim 1, wherein said implant is substantially rigid.

4. The method of claim 3, wherein said implant is made of a metal material.

5. The method of claim 4, wherein said implant is made of a cobalt chrome material.

\* \* \* \* \*